United States Patent [19]

Sone et al.

[11] Patent Number: 5,132,000
[45] Date of Patent: Jul. 21, 1992

[54] CALIBRATION SOLUTION AND CALIBRATION METHOD FOR SENSOR

[75] Inventors: Atsushi Sone; Norihiko Ushizawa; Takeshi Shimomura, all of Fuji, Japan

[73] Assignee: Terumo Kabushiki Kaisha, Tokyo, Japan

[21] Appl. No.: 411,114

[22] Filed: Sep. 22, 1989

[30] Foreign Application Priority Data

Sep. 24, 1988 [JP] Japan ................. 63-239489

[51] Int. Cl.⁵ .......................................... G01N 27/26
[52] U.S. Cl. ........................... 204/416; 204/153.1; 204/153.21; 204/400
[58] Field of Search ............. 204/153.1, 400, 153.21, 204/416; 436/18, 8, 10, 7

[56] References Cited

U.S. PATENT DOCUMENTS

| | | |
|---|---|---|
| 3,365,376 | 1/1968 | Weyland ................. 204/400 |
| 3,556,950 | 1/1971 | Dahms ................. 204/153.1 |
| 3,681,255 | 8/1972 | Wilfore ................. 204/153.1 |
| 3,941,565 | 3/1976 | Schwartz ................. 204/153.21 |
| 4,544,455 | 10/1985 | Eisenhardt ................. 204/416 |
| 4,626,512 | 12/1986 | Okue et al. ................. 436/18 |

FOREIGN PATENT DOCUMENTS 2436991 9/1979 France .

Primary Examiner—John Niebling
Assistant Examiner—Bruce F. Bell
Attorney, Agent, or Firm—Burns, Doane, Swecker & Mathis

[57] ABSTRACT

A calibration solution, which is used when measuring the ion concentration of solution under examination such as blood or other body fluids using a pH sensor or the like ion sensor with a solid electrode, is prepared by adding NaCl to a standard buffer solution and thus setting the ionic strength of the solution to be substantially identical with the ionic strength of solution under examination. A sensor calibration method is also disclosed, in which at least two reference calibration solutions having different pH values are prepared, the electromotive force of the sensor in these calibration solutions is measured by immersing the sensor in the solutions, and a calibration formula is produced from the electromotive force for the pH values of the reference calibration solutions. A predetermined amount of bicarbonate buffer solution is added to the calibration solution to maintain a substantially constant ionic strength of the solution, thus permitting simultaneous calibration of an ion sensor and a gas sensor.

15 Claims, 5 Drawing Sheets

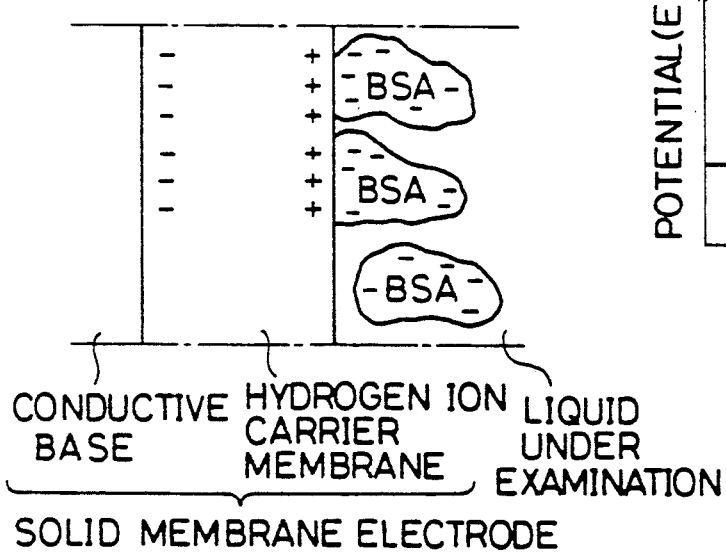
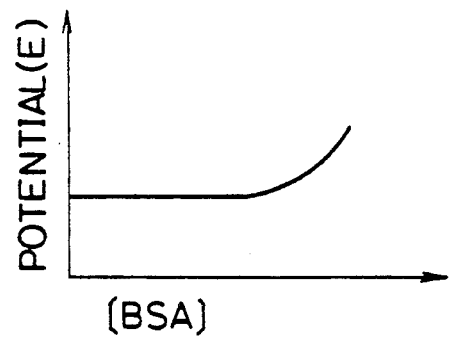
FIG.6(a)
FIG.6(b)

CALIBRATION SOLUTION AND CALIBRATION METHOD FOR SENSOR

BACKGROUND OF THE INVENTION

This invention relates to a calibration solution and a calibration method used when measuring ion concentration in medical fields, clinical fields and biochemical fields dealing with blood and other body fluids and ion concentration in variable partial gas pressure systems using an ion sensor or gas sensor having solid electrodes.

When measuring the pH and partial gas concentration as of blood and other body fluids as a solution under examination, use is usually made of a standard buffering solution prescribed in the JIS (Japanese Industrial Standard) standards and NBS standards (National Bureau Standard), e.g., phthalic acid salt, phosphate, etc., and measurement was done by using glass electrodes. In this case, electrode of the same kind and same structure as the inner electrode of the glass electrode is used as the reference electrode.

It is found that ion selective electrodes as well as minute solid microelectrodes and the like can be extensively utilized for medical sensors, and there are indications of practical use of pH sensors and other ion sensors in the field of clinical chemistry and artificial organ control monitors. When it is intended to apply sensors in the medical field, high accuracy measurement and temperature compensation requirement levels are higher than in the case of the general analysis, and it is difficult to meet these levels.

pH sensors and other ion sensors measure the electrode potential difference corresponding to ion activity. The ion activity is the product of the ion concentration and activity coefficient. Usually, a glass membrane electrode is used as a pH electrode, but it can not meet the definition of pH given as $$pH = -\log a_{H^+} \tag{1}$$

This is so because it is impossible to obtain this value strictly due to the presence of liquid junction potential in contrast to the electrode solution section and an ion activity coefficient which is incapable of measurement. For this reason, a pH value which can be mathematically calculated from pH values of the inner solution and outer measurement solution, is defined and used, which is given as $$pH_x - pH_s = \frac{E_x - E_s}{(2.303RT/F)} \tag{2}$$

where R is the gas constant, T is the absolute temperature, F is the Farady constant, $E_x$ and $E_s$ are battery electromotive forces in solutions X and S. The battery is composed of Pt; $H_2$ solution X or S/saturated KCl solution, saturated caromel electrode.

Here, a solution with $pH_s$ is a standard solution. As the standard solution, a 0.05M potassium hydrogen phthalate solution is used, and the pH there is defined to be 3.998 (0° C., 4.000) at 15° C. This standard conforms to NBS and is adopted in Japan.

With a membrane electrode other than a glass membrane, the measurement of the electrode potential difference on the membrane surface is influenced by the coexistent matter in the solution under examination such as other ions than the subject of measurement, protein, and amino acids. This is so because the electrode potential difference is measured to calculate pH on the basis of the definition of equation (1).

In the measurement where the solution under examination is blood or like body fluids, a high accuracy of measurement is required despite slight ion concentration changes. Therefore, with calibration of a sensor on the basis of the usual method of measurement as noted above, the measurement errors are too large to expect a high accuracy sensor, particularly in the medical field.

SUMMARY OF THE INVENTION

An object of the invention, accordingly, is to provide a calibration solution and a calibration method, which permit high accuracy measurement using sensors in medical and other fields.

To attain the above objective of the invention, the invention is predicated in the fact that the activity coefficient noted above is determined by the charge of ions and total ionic the strength in the solution.

The ionic strength I and the activity coefficient are related to each other as a Debye-Huckel threshold equation $$-\log(\gamma_i) = \frac{AZ_i^2 \sqrt{I}}{1 + B a_i \sqrt{I}} \tag{3}$$

where A and B are constants determined by the dielectric constant and the temperature of the solvent, $Z_i$ represents ion valency, I is ionic strength and $a_i$ is the effective radius of a hydration ion.

The activity coefficient of a certain ion depends on the total ionic strength of that solution. Therefore, the ionic strength, i.e., activity coefficient, varies with the changes in the concentrations of coexistent ions other than the measurement ion even if the measurement ion concentration is constant. According to the invention, the ionic strength is set to be substantially identical with the ionic strength of the solution under measurement.

According to the invention, there is basically provided a calibration solution for a sensor which consists of a solid electrode for measuring ion concentration of a solution under examination, in which NaCl is added to a standard buffer solution to provide an ionic strength substantially identical with the ionic strength of the solution under examination.

The calibration solution of the above constitution permits measurement with less error. Particularly, the invention can be more suitably utilized in medical and like fields, in which the solution under examination is blood or like body fluids subject to less ion concentration changes According to the invention, there is also provided a calibration method for calibrating a sensor, in which at least two reference calibration solutions having different pH values are prepared, the electromotive forces of the sensor in these reference calibration solutions are measured by immersing the sensor in these solutions, and a calibration formula (calibration curve) from the electromotive forces with respect to the pH values of the reference calibration solutions.

By adopting the calibration solution noted above it is possible to obtain high accuracy measurement using a pH sensor or like sensor.

According to the invention, there is further provided a calibration solution for calibrating a sensor in case of measuring partial gas pressure as well as ion concentration of a solution under examination containing carbon dioxide gas and/or oxygen gas, in which a predetermined quantity of bicarbonate buffer solution is added to the standard buffer solution to maintain a substantially constant ion concentration as well as adding NaCl to set an ionic strength substantially identical with the ionic strength of the solution under examination.

This calibration solution can be utilized for calibrating a carbon dioxide gas sensor as well as a pH sensor or like ion sensor, that is, it is possible to obtain a simultaneous calibration solution permitting high accuracy simultaneous measurement.

According to the invention, there is further provided a calibration method for calibrating an ion sensor and a gas sensor, in which at least two reference calibration solutions having different pH values and partial gas pressure values are prepared, the electromotive forces of these sensors in these reference calibration solutions are measured by immersing the sensors in the solutions, and calibration formulas are formed by plotting the electromotive forces of the sensors for the pH values and partial gas pressure values for gas sensor.

By adopting this calibration method, the measurement of ion concentration with a pH sensor or like ion sensor and measurement of partial gas pressure of carbonate or like gas with a gas sensor can be done simultaneously and with better accuracy than conventional calibration formulas.

DETAILED DESCRIPTION OF THE PREFERRED EMBODIMENTS

Figure 1:
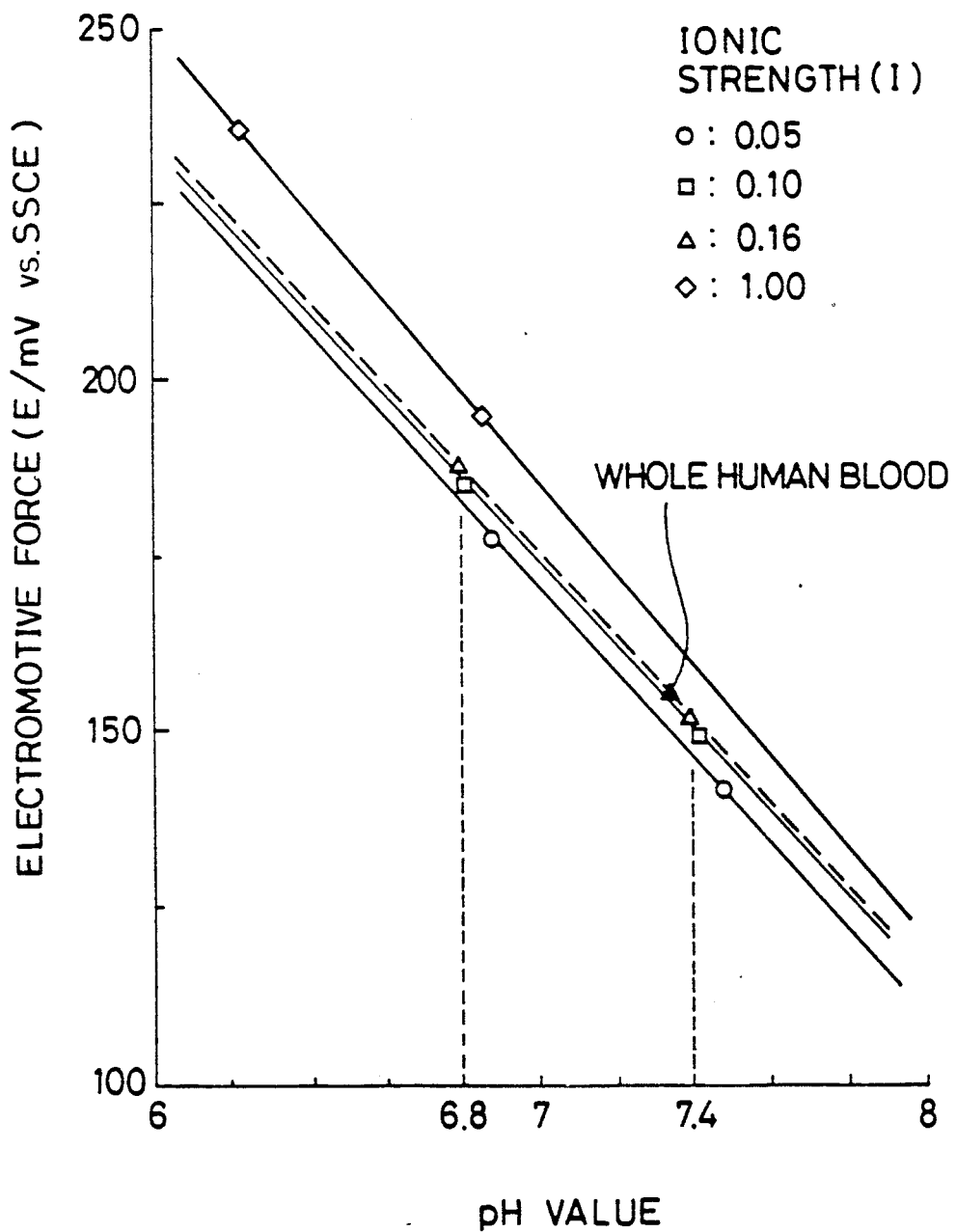
FIG. 1 is a graph showing the relation between the sensor electromotive force and pH value produced according to the ionic strengths of different examples in a first embodiment of the invention.

According to the invention, a first standard buffer solution is prepared by using a mixture solution composed of Na$_2$HPO$_4$ (27.2 mEq/l)/NaH$_2$PO$_4$ (6.8 mEq/l) and Na$_2$HPO$_4$ (22.5 mEq/l)/NaH$_2$PO$_4$ (22.5 mEq/l) of phosphate buffer solution system with respective pH values of 7.4 and 6.8. By adding NaCl to the standard buffer solution, the ionic strength is changed. That is, even if the Na$^+$ ion concentration in the phosphate buffer solution is constant, the ionic strength is changed with the dissociation of the coexistent NaCl solution as given by an equation $$pH = pK_a + \log\frac{[HPO_4^{2-}]}{[H_2PO_4^-]} - (2n-1)\left\{0.5091\left(\frac{\sqrt{I}}{1+\sqrt{I}} - 0.1I\right)\right\} \quad (4)$$

where: $I$ (ionic strength) $= \frac{1}{2}\Sigma Z_i^2 \cdot C_i$ pKa: dissociation constant of phosphate
Zi: Ion valency
Ci: Ion mol concentration
n: an index, which is given for buffer solution as
$H_nA^{n-} \rightleftharpoons H_{n-1}A^{(nH)-} + H^+$
n = 1 when
$H_2PO_4^- \rightleftharpoons HPO_4^{2-} + H^+$ At least two standard buffer solutions having an ionic strength substantially identical with that of solution under examination and having different pH values are prepared on the basis of equation (4), and a calibration formula is formed by plotting the electromotive forces of a pH sensor or the like in these standard buffer solutions by immersing the sensor in the solutions.

Thus, a calibration solution and a calibration method are obtained for pH sensors and like ion sensors.

Where the whole human blood is dealt with as a solution under examination, the ionic strength is 0.08 to 0.18 although it varies with individuals. In this case, therefore, a calibration solution may be prepared which has an identical ionic strength.

Secondly, the preparation of a calibration solution and a method of calibration, which can meet an aim of simultaneously calibrating an ion sensor and a gas sensor for measuring ion concentration and partial gas pressure, respectively, will now be described.

When CO$_2$ gas, for example, is dissolved in solution, for instance, the [H$^+$], i.e., pH, is changed such that $$CO_2 + H_2O \rightleftharpoons H_2CO_3 \rightleftharpoons HCO_3^- + H^+$$

By using bicarbonate buffer solution like phosphate buffer solution, the pH of the solution can be held constant in the presence of CO$_2$.

In the bicarbonate buffer solution the carbonate dissociation constant K is given as $$K = \frac{[HCO_3^-][H^+]}{[CO_2]}$$

From the Henry's law, $$K = \frac{[HCO_3^-][H^+]}{\alpha P_{CO_2}}$$

where:
$\alpha$: dissolution coefficient
$P_{CO_2}$: partial pressure of CO$_2$
By taking the logarithm of both sides, $$pH = pK + \log\frac{[HCO_3^-]}{\alpha P_{CO_2}} \quad (5)$$

It will be seen that for the preparation of a calibration solution with a constant pH it is necessary to maintain a constant concentration of [HCO$_3^-$] and a constant partial pressure $P_{CO_2}$.

The concentration of [HCO$_3^-$] may be obtained from the intersection between equations (4) and (5) by varying it with the standard buffer solution system of pH values of 7.4 and 6.8 while holding constant the [HPO$_4^{2-}$]/[H$_2$PO$_4^-$] in equation 4 and $P_{CO_2}$ in equation (5).

The invention is further predicated in charges induced on the membrane surface of a solid membrane electrode by charges on ions and protein dissolved in solution under examination.

More specifically, it is found that charges on ions and/or protein in the solution under examination have influence on the surface of the solid membrane. It is experimentarily confirmed that this phenomenon is due to the fact that NaCl electrolyte is predominant. The invention seeks to provide a calibration solution for a sensor, with which a system obtained by adding NaCl to a standard buffer solution and a system of ions and/or protein dissolved in the solution under examination are made identical in the status of charges to that of charges induced on solid membrane surface.

Now, a first embodiment of the invention, concerning calibration of a sole pH sensor, a second embodiment concerning simultaneous calibration of a pH sensor and a gas sensor, and a third embodiment concerning calibration for making the ionic strength identical with the status of charges on ions and/or protein dissolved in the solution under examination will now be described with standard to the accompanying drawings.

FIRST EMBODIMENT

As shown in Tables 1-A and 1-B, calibration solution compositions with different ionic strengths of 0.05, 0.10, 0.16 and 1.0 were calculated according to equation (4) as Examples 1 to 8 in two groups, one with pH in the neighborhood of 7.4 (Table 1-A) and the other with pH in the neighborhood of 6.8 (Table 1-B).

The ratio $Na_2HPO_4/NaH_2PO_4$ in the standard buffer solution was set to 4/1 in Examples 1 to 4 and to 1/1 in Examples 5 to 8.

By plotting the relation between the electromotive force and pH value from the above tables, a calibration curve corresponding to each ionic strength as shown in FIG. 1 can be obtained.

TABLE 1-A

| | $\frac{Na_2HPO_4}{NaH_2PO_4}$ (mEq/l) | NaCl (mEq/l) | I | $\gamma_i$ | pH | E (mV) |
|---|---|---|---|---|---|---|
| | (around pH = 7.4) | | | | | |
| 1 | 27.2/6.8 | 5.8 | 0.05 | 0.812 | 7.473 | 141.05 |
| 2 | 27.2/6.8 | 11.6 | 0.10 | 0.766 | 7.417 | 149.18 |
| 3 | 27.2/6.8 | 71.6 | 0.16 | 0.736 | 7.403 | 151.1 |
| 4 | 27.2/6.8 | 911.6 | 1.0 | 0.689 | 6.842 | 195.59 |

TABLE 1-B

| | $\frac{Na_2HPO_4}{NaH_2PO_4}$ (mEq/l) | NaCl (mEq/l) | I | $\gamma_i$ | pH | E (mV) |
|---|---|---|---|---|---|---|
| | (around pH = 6.8) | | | | | |
| 5 | 22.5/22.5 | 5.0 | 0.05 | 0.812 | 6.887 | 177.14 |
| 6 | 22.5/22.5 | 10 | 0.10 | 0.766 | 6.815 | 185.15 |
| 7 | 22.5/22.5 | 70 | 0.16 | 0.736 | 6.801 | 187.24 |
| 8 | 22.5/22.5 | 910 | 1.0 | 0.689 | 6.239 | 254.88 |

TABLE 1-C

| Calibration Solution | A/B | NaCl |
|---|---|---|
| I | A/B = 4/1 0.001~4 M | 0.001~4 M |
| II | A/B = 1/1 0.001~4 M | 0.001~4 M |

(A: $Na_2HPO_4$, B: $NaH_2PO_4$)

Specifically, when total human blood (with an ionic strength of about 0.15) is dealt with as the solution under examination, the electromotive forces of 151.1 and 187.24 mV obtained from pH sensor in calibration solutions I and II in Examples 3 and 7, respectively, are plotted, and a calibration curve with an ionic strength of 0.16, shown by dashed line in FIG. 1 is used.

Suitable ranges of components of calibration solutions I and II are as in Table 1-C as above.

Electromotive force obtained from a pH sensor with saturated sodium chloride caromel electrode (SSEC) as electrode potential pair in case of total human blood was 153.30 mV, and pH at this time measured at a temperature of 37° C. using a HL-30 gas monitor manufactured by Radiometer Co., Ltd. was 7.367.

The result copied on the calibration curve of FIG. 1, as shown by the black triangle mark, was identical with the ionic strength of I=0.16 on the calibration curve.

Where total human blood is the solution under examination, the ionic strength varies with literatures and fluctuates in actual measurements, and this is thought to be due to differences of individuals.

The range of fluctuation may be thought to be 0.08 to 0.18, and a calibration curve may be formed with respect to ionic strength values in this range.

SECOND EMBODIMENT

Calibration solutions for simultaneous calibration of ion sensor and gas sensor were prepared as Examples 9 to 18 shown in Tables 2-A and 2 B below. Calibration solution I was used for Examples 9 to 13, and calibration solution II for Examples 14 to 18. $NaHCO_3$ was added to these calibration solutions, and the calibration solution compositions were calculated on the basis of equation (5).

Mixture gas of $CO_2$ and $O_2$ was dissolved in a ratio of $P_{CO2}=36.1$ mmHg and $P_{O2}=35.2$ mmHg in the solutions of Examples 9 to 13 and in a ratio of $P_{CO2}=79.0$ mmHg and $P_{O2}=142.6$ mmHg in the case of Examples 14 to 18.

The amount of $NaHCO_3$ in calibration solution suited for simultaneous calibration of ion sensor and gas sensor is determined as follows.

Figure 2:
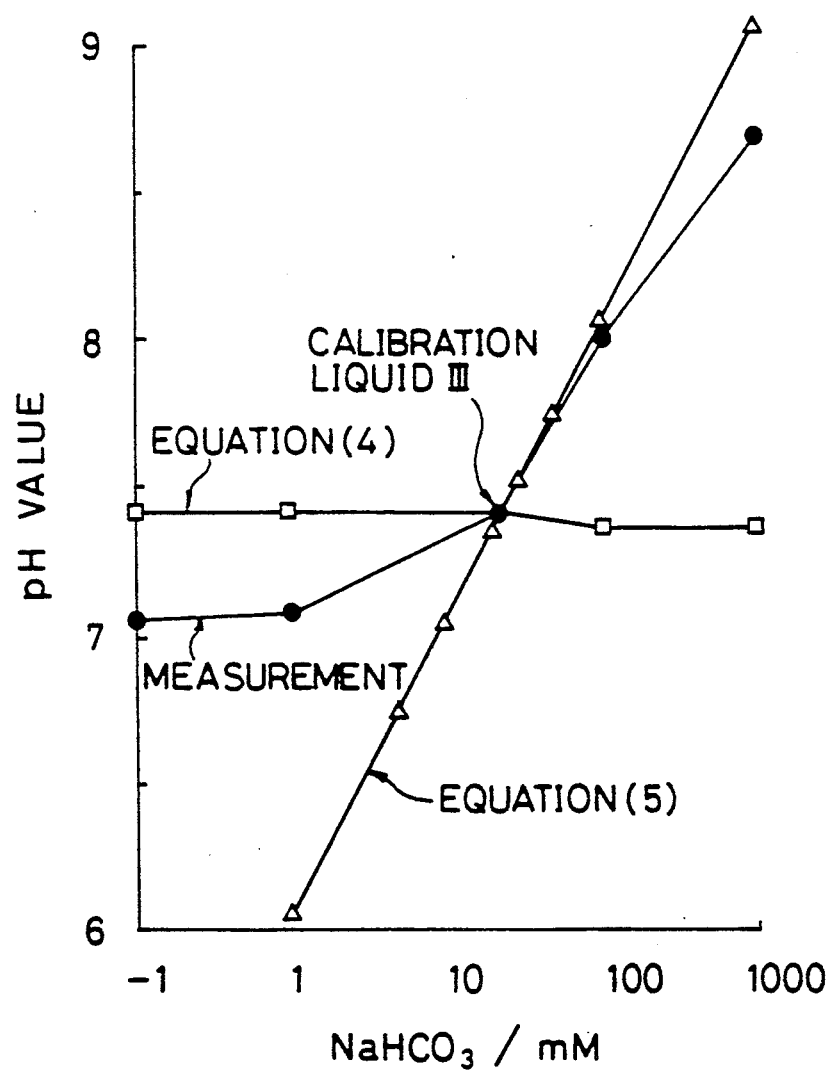
FIGS. 2 and 3 are graphs for determining NaHCO$_3$ concentrations at different pH value suited for simultaneous calibration of ion sensor and gas sensor in a second embodiment of the invention.
Figure 3:
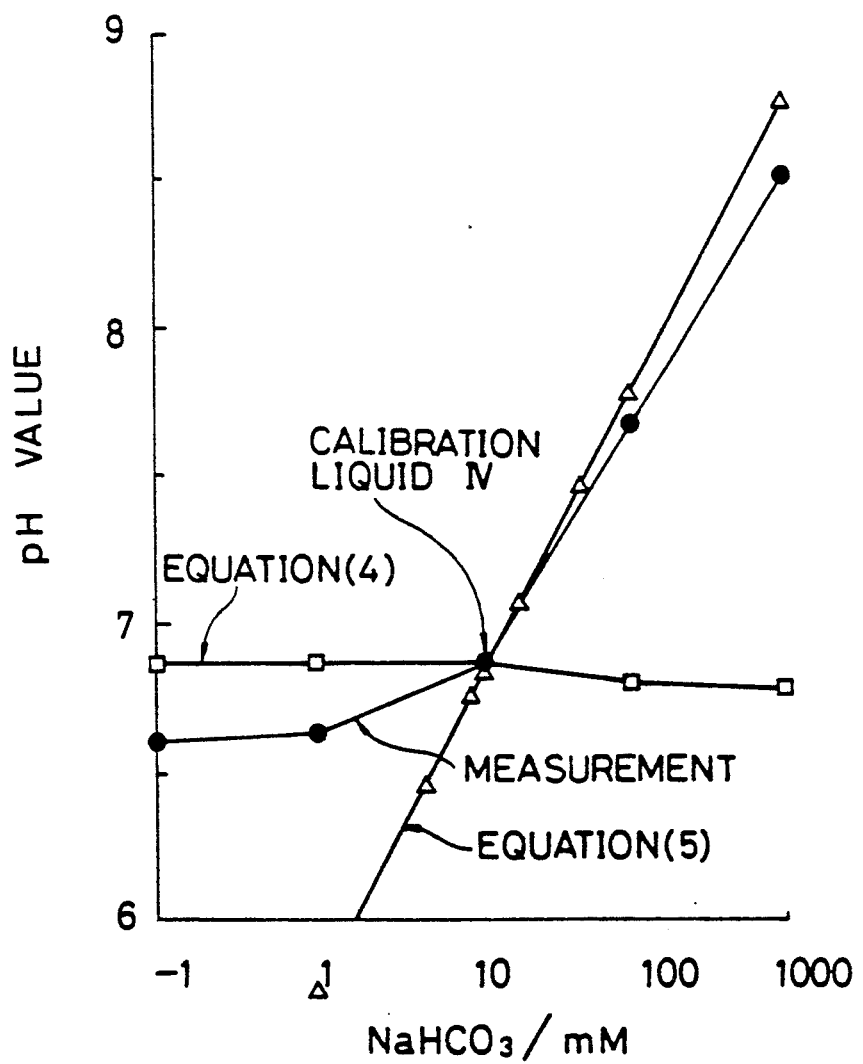

As shown in FIGS. 2 and 3, by considering equations (4) and (5) the concentration of $HCO_3^-$ in solution was determined from the intersection between curves of equations (4) and (5) by varying $[HCO_3^-]$ alone in the neighborhood of pH=7.4 (FIG. 2) and in the neighborhood of pH=6.8 (FIG. 3) while holding constant $[HPO_4^{2-}]/[H_2PO_4^-]$ in equation 4 and $P_{CO2}$ in equation (5).

TABLE 2-A

| | $\frac{Na_2HPO_4}{NaH_2PO_4}$ (mEq/l) | NaCl (mEq/l) | $HCO_3^-$ (mEq/l) | pH | E (mV) | I | $\gamma_i$ |
|---|---|---|---|---|---|---|---|
| | (around pH = 7.4, $NaHCO_3$ added) | | | | | | |
| 9 | 27.2/6.8 | 71.6 | 0 | 7.051 | 172.3 | 0.16 | 0.736 |

TABLE 2-A-continued (around pH = 7.4, NaHCO₃ added)

| Na₂HPO₄/NaH₂PO₄ (mEq/l) | NaCl (mEq/l) | HCO₃⁻ (mEq/l) | pH | E (mV) | I | $\gamma_i$ |
| --- | --- | --- | --- | --- | --- | --- |
| 10 | 27.2/6.8 | 70.6 | 1 | 7.072 | 171.0 | 0.16 | 0.736 |
| 11 | 27.2/6.8 | 51.6 | 20 | 7.385 | 152.2 | 0.16 | 0.736 |
| 12 | 27.2/6.8 | 49.2 | 22.4 | 7.414 | 150.5 | 0.16 | 0.736 |
| 13 | 27.2/6.8 | 21.6 | 50 | 7.621 | 138.1 | 0.16 | 0.736 |

TABLE 2-B (around pH = 6.8, NaHCO₃ added)

| Na₂HPO₄/NaH₂PO₄ (mEq/l) | NaCl (mEq/l) | HCO₃⁻ (mEq/l) | pH | E (mV) | I | $\gamma_i$ |
| --- | --- | --- | --- | --- | --- | --- |
| 14 | 22.5/22.5 | 70 | 0 | 6.598 | 199.4 | 0.16 | 0.736 |
| 15 | 22.5/22.5 | 69 | 1 | 6.627 | 197.7 | 0.16 | 0.736 |
| 16 | 22.5/22.5 | 58.2 | 11.8 | 6.860 | 183.7 | 0.16 | 0.736 |
| 17 | 22.5/22.5 | 50 | 20 | 6.935 | 179.2 | 0.16 | 0.736 |
| 18 | 22.5/22.5 | 20 | 50 | 7.208 | 168.8 | 0.16 | 0.736 |

TABLE 2-C

| Calibration Solution | A/B | NaCl | NaHCO₃ | $P_{CO_2}$ | $P_{O_2}$ |
| --- | --- | --- | --- | --- | --- |
| III | A/B = 4/1<br>0.005~4 M | 0.001~4 M | 0.001~0.1 M | 0~80 mmHg | 0~100 mmHg |
| IV | A/B = 1/1<br>0.005~4 M | 0.001~4 M | 0.001~0.1 M | 40~120 mmHg | 50~760 mmHg |

(A: Na₂HPO₄, B: NaH₂PO₄)

Black circle marks on the curves represent actual measurement values.

Examples 12 was determined to be appropriate as calibration solution III, and Example 16 as calibration solution IV.

Calibration curves for pH sensor, carbon dioxide gas sensor and oxygen gas sensor can be formed by measuring the electromotive forces of the pH sensor and carbon dioxide gas sensor and current in the oxygen gas sensor in both the calibration solutions III and IV, plotting the electromotive forces of the pH sensor and carbon dioxide gas sensor for the pH values and $P_{CO_2}$ values of the solutions III and IV and plotting the current in the oxygen gas sensor for the $P_{O_2}$ values.

Suitable ranges of components of calibration solutions III and IV are as in Table 2-C as above.

By obtaining calibration solution in the above way, producing calibration curves by considering a measurement temperature range of 37° C. to 30° C., and memorizing electrode characteristics of sensor at this time, it is possible to provide calibration solution and calibration system suitable for continuous monitoring in biomedical engineering.

THIRD EMBODIMENT

Figure 4A:
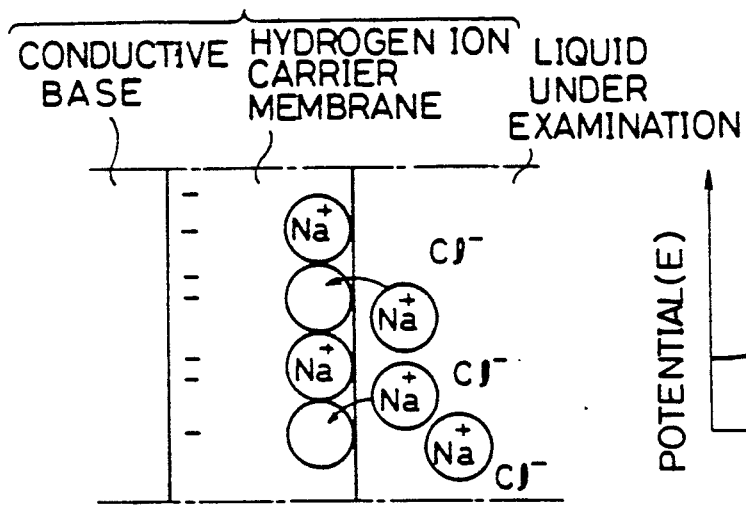
FIGS. 4(a) and (b) to 6(a) and (b) are views of the neighborhood of membrane surface for explaining the status of charges induced on electrode membrane surface by ions and/or protein in a third embodiment of the invention together with showing of graphs.
Figure 4B:
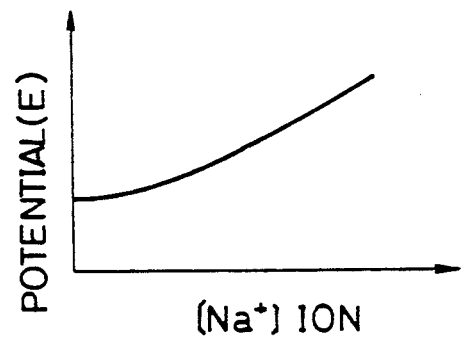
Figure 5A:
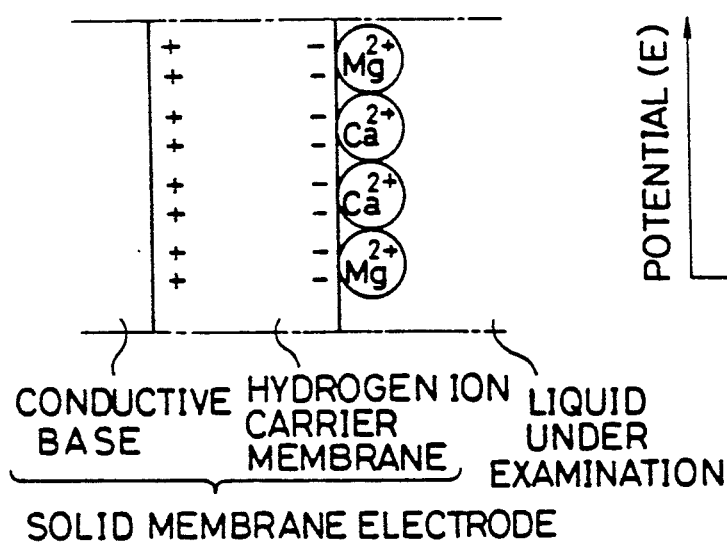
Figure 5B:
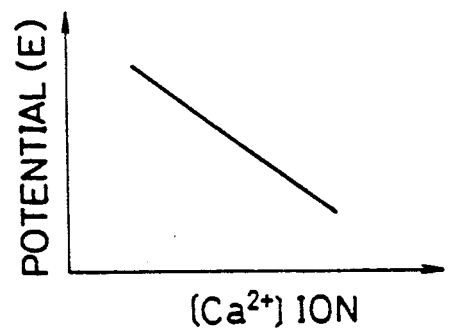

FIGS. 4 to 6 illustrate the status of charges induced on solid membrane electrode surface by ions and/or protein dissolved in solution under examination.

FIG. 4 shows the behavior of sodium ions in the solution under examination containing NaCl with respect to the film surface of an hydrogen ion carrier membrane of a solid membrane electrode immersed in the solution under examination. As shown in (a), sodium ions near the membrane surface are captured on the membrane surface to induce positive charges, while inducing negative charges on the carrier membrane of electrode on the side of conductive base.

The membrane surface potential E and sodium ion concentration are related as shown in (b), and the calibration solution used here is prepared in comformity to the status of charges induced on the membrane surface.

FIG. 5 shows behavior in case where magnesium and calcium ions are dissolved in the solution under examination. As shown in (a), these ions induce negative charges on the hydrogen carrier membrane surface, and the calcium ion concentration, for instance, and membrane surface potential E are related substantially linearly as shown in (b). The same applies in the case of magnesium ions.

The calibration solution in this case, therefore, is prepared such as to conform to the status of charges induced in the membrane surface from the consideration of the relation shown in the graph.

FIG. 6 concerns a case, in which the solution under examination is a protein solution containing dissolved bovine serum albumin (BSA) as protein.

It will be seen that a calibration solution concerning a protein solution as above as the solution under consideration is prepared such as to conform to the status of charges from the consideration of the relation shown in (b).

Examples of electrode subject to the influence of adsorbed protein are ISFET electrodes, platinum electrodes, SnO₂ electrodes and glassy carbon electrodes. With ISFET electrodes, in which glass electrode and sensor membrane are covered with glass, variation of protein concentration caused no potential changes.

What is claimed is:

1. A calibration solution for a sensor with a solid electrode for measuring ion concentration of a solution under examination, comprising a standard buffer solution which comprises a mixture solution of Na₂HPO₄ and NaH₂PO₄ in a 1 to 1 ratio, and with NaCl being added to said buffer solution to provide an ionic strength substantially identical with the ionic strength of said solution under examination.

2. A calibration solution for a sensor with a solid electrode for measuring ion concentration of a solution under examination, comprising a standard buffer solution which comprises a mixture solution of Na₂HPO₄ and NaH₂PO₄ in a 4 to 1 ratio, and with NaCl being added to said buffer solution to provide an ionic strength substantially identical with the ionic strength of said solution under examination.

3. A calibration solution for a sensor with a solid electrode for measuring ion concentration of a solution under examination, comprising a standard buffer solution, and with NaCl being added to said buffer solution to provide an ionic strength in the range of 0.08 to 0.18 which is substantially identical with the ionic strength of said solution under examination.

4. A calibration method for calibrating an ion sensor comprising the steps of:

setting an ionic strength which is substantially identical with the ionic strength of a solution under examination by adding NaCl to a standard buffer solution which comprises a mixture of $Na_2HPO_4$ and $NaH_2PO_4$ in a 1 to 1 ratio while preparing at least two reference calibration solutions having different pH values;

measuring the electromotive force in each of said reference calibration solutions by immersing said sensor in each of said solutions; and producing a calibration formula from the electromotive forces with respect to the pH values of each of said reference calibration solutions.

5. A calibration method for calibrating an ion sensor comprising the steps of:

setting an ionic strength which is substantially identical with the ionic strength of a solution under examination by adding NaCl to a standard buffer solution which comprises a mixture of $Na_2HPO_4$ and $NaH_2PO_4$ in a 4 to 1 ratio while preparing at least two reference calibration solutions having different pH values;

measuring the electromotive force in each of said reference calibration solutions by immersing said sensor in each of said solutions; and producing a calibration formula from the electromotive forces with respect to the pH values of each of said reference calibration solutions.

6. A calibration solution for a sensor with a solid electrode for measuring the ion concentration of a solution under examination which comprises a standard buffer solution comprised mainly of a phosphate buffer which buffer is a mixture composed of $Na_2HPO_4$ and $NaH_2PO_4$, and with NaCl being added to said buffer solution to permit the solid membrane surface of said electrode to be held at equilibrium potential.

7. A calibration solution for a sensor for simultaneously calibrating an ion sensor and a gas sensor, these sensors being provided with solid electrodes with respect to the ion concentration and dissolved gas concentration in solution under examination;

NaCl being added to said standard buffer solution to provide an ionic strength substantially identical with the ionic strength of solution under examination, a predetermined quantity of bicarbonate buffer solution being added to maintain the ion concentration substantially constant.

8. The calibration solution for a sensor according to claim 7, wherein said bicarbonate buffer solution is $NaHCO_3$.

9. The calibration solution according to claim 8, which contains predetermined quantities of carbon and oxygen gases.

10. The calibration solution according to claim 9, wherein said sensor is a carbon dioxide gas sensor.

11. The calibration solution for a sensor according to claim 9, wherein said sensor is an oxygen gas sensor.

12. A calibration method for simultaneously calibrating an ion sensor and a gas sensor comprising the steps of:

preparing at least two standard buffer solutions having different pH values and partial gas pressure values by adding NaCl for setting an ionic strength substantially identical with the ionic strength of solution under examination and also adding a bicarbonate buffer solution for stabilizing the pH value;

measuring the electromotive forces of said ion and gas sensors in said reference calibration solutions by immersing said sensors in said solutions; and forming calibration formulas by plotting the electromotive forces of said ion gas sensors for the pH values and partial gas pressure values of said standard buffer liquids, respectively.

13. The calibration method according to claim 12, wherein said ion and gas sensors are respectively a pH sensor and a carbon dioxide gas sensor.

14. A calibration method for simultaneously calibrating a pH sensor, a carbon dioxide gas sensor and an oxygen gas sensor comprising the steps of:

preparing at least two standard buffer solutions having different pH values, partial carbon dioxide gas pressure values and partial oxygen pressure values by adding NaCl for setting an ionic strength substantially identical with the ionic strength of solution under examination and also adding a bicarbonate buffer solution for stabilizing the pH value;

measuring the electromotive forces of said pH and carbon dioxide gas sensors and also the current in said oxygen sensor in said reference calibration solutions by immersing said sensors in said solutions; and forming calibration formulas by plotting the electromotive forces of said pH and carbon gas sensors for the pH values and partial carbon dioxide gas pressure values of said reference calibration solutions and also forming a calibration formula by plotting the current value of said oxygen sensor for the partial oxygen pressure value.

15. The calibration method according to claim 12, wherein said bicarbonate buffer solution is $NaHCO_3$.

* * * * *